United States Patent [19]

Sioli

[11] Patent Number: 5,959,154
[45] Date of Patent: Sep. 28, 1999

[54] PROCESS FOR HETEROGENEOUS EXOTHERMIC SYNTHESIS OF FORMALDEHYDE

[75] Inventor: Giancarlo Sioli, Cernobbio, Italy

[73] Assignee: Floriall Holdings Limited, Dublin, Ireland

[21] Appl. No.: 08/930,628

[22] PCT Filed: Apr. 9, 1996

[86] PCT No.: PCT/EP96/01516

§ 371 Date: Dec. 1, 1997

§ 102(e) Date: Dec. 1, 1997

[87] PCT Pub. No.: WO96/32189

PCT Pub. Date: Oct. 17, 1996

[30] Foreign Application Priority Data

Apr. 11, 1995 [CH] Switzerland .......................... 1042/95

[51] Int. Cl.⁶ .................................................. C07C 45/29
[52] U.S. Cl. ...................... 568/472; 568/448; 568/487; 568/422; 422/196; 29/401.1
[58] Field of Search .................................. 568/448, 422, 568/472, 487; 422/196; 29/401.1

[56] References Cited

U.S. PATENT DOCUMENTS

| 2,504,402 | 10/1950 | Field . | |
|---|---|---|---|
| 2,512,562 | 10/1950 | Cummings . | |
| 4,372,920 | 2/1983 | Zardi | 422/148 |
| 4,755,362 | 7/1988 | Zardi | 422/148 |
| 4,904,453 | 2/1990 | Zardi | 422/148 |
| 4,952,375 | 8/1990 | Zardi | 422/148 |

FOREIGN PATENT DOCUMENTS

| 3318098 | 11/1984 | Germany . |
|---|---|---|
| 60-110328 | 6/1985 | Japan . |
| 2055606 | 3/1981 | United Kingdom . |
| 2122102 | 1/1984 | United Kingdom . |

*Primary Examiner*—Shailendra Kumar
*Assistant Examiner*—Sreeni Padmanabhan
*Attorney, Agent, or Firm*—Sughrue, Mion, Zinn, Macpeak & Seas, PLLC

[57] ABSTRACT

A process for the heterogeneous exothermic synthesis of formaldehyde, in particular in reactors of the type comprising a plurality of adiabatic catalytic beds connected in series, provides the step of flowing the gaseous reagents across at least one of the catalytic beds with substantially radial flow.

7 Claims, 2 Drawing Sheets

PROCESS FOR HETEROGENEOUS EXOTHERMIC SYNTHESIS OF FORMALDEHYDE

This is the us National stage Application of PCT/EP96/01516 filed Apr. 9, 1996 now WO96/32189 published Oct. 17, 1996.

DESCRIPTION

1. Field of Application

The present invention relates to a process for heterogeneous exothermic synthesis of formaldehyde in excess oxygen, in particular in synthesis reactors of the type comprising a plurality of adiabatic catalytic beds connected in series, with the process comprising the steps of:

feeding gaseous reagents comprising methanol and excess oxygen to a first of said catalytic beds;

flowing said gaseous reagents across the catalytic beds to subject the methanol to partial oxidation.

The present invention also relates to a reactor for heterogeneous exothermic synthesis of formaldehyde.

In the description given below and in the following claims, the term: 'adiabatic catalytic bed', is understood to mean a bed containing catalyst in which the synthesis reaction takes place at a substantially constant pressure without heat removal.

In the field of heterogeneous exothermic synthesis of formaldehyde, the requirement on the one hand of increasing the productive capacity of the synthesis reactors and on the other hand of reducing the risks of explosion of the gaseous reagents comprising methanol and oxygen in excess, while holding down energy consumption and investment and maintenance costs, is increasingly felt.

2. Prior Art

For the purpose of meeting the above mentioned requirement, tubular reactors with heat removal by passage of a cooling liquid circulating outside the tubes have become increasingly accepted.

This type of reactor consisting of a plurality of small-diameter tubes filled with catalyst is very complicated to construct and has limited production capacity.

In the second half of the nineteen-eighties there was proposed by the Boreskov Institute of Catalysis of Novosibirsk, Russia, the adoption of a formaldehyde synthesis process in which the gaseous reagents comprising methanol and excess oxygen are reacted in a plurality of adiabatic catalytic beds connected in series.

The gaseous reagents cross the catalytic beds with axial flow. Between the outlet from a bed and the inlet to the following bed the gas flow is appropriately cooled by heat exchange in suitable heat exchangers.

The above mentioned process permits provision of reactors of large size and having a production capacity higher than that obtainable with the conventional tubular reactors, since it is possible to increase the reaction space and the flowrate of the gaseous reagents and it is possible to improve the selectivity of the oxidation reaction of the methanol.

If on the one hand this type of solution proves to be advantageous as compared with tubular reactors, on the other hand the production capacity of the synthesis reactor remains limited by the concentration of methanol contained in the gaseous reagents entering the reactor.

As known, this concentration must be held below certain values which generally do not exceed 6%–9% by volume depending on the oxygen concentration, which can vary between 5% and 21% by volume, to avoid the possible formation of explosive or inflammable mixtures with the oxygen.

A relatively low concentration of methanol is also preferable for limiting the amplitude of temperature variations in the catalytic mass. Indeed, at temperatures over 300° C. there is the risk of deterioration of the catalyst with resulting reduction of its useful life and a drastic increase in the undesired secondary reactions which lead to direct degradation of the methanol or of the formaldehyde produced.

In addition, the embodiment of a large synthesis reactor with large gas flowrates of the type developed by the Boreskov Institute of Catalysis involves considerable technical difficulties, high investment costs and high energy consumption.

For the exothermic synthesis of compounds like ammonia or methanol, adiabatic reactors of the radial or axial/radial type are known. See for instance GB-A-2 722 702 or JP-A-60 770 328.

SUMMARY OF THE INVENTION

The technical problem underlying the present invention is to increase the production capacity of formaldehyde synthesis reactors while reducing the risks of explosion of the gaseous reagents comprising methanol and excess oxygen while holding down energy consumption and investment and maintenance costs.

This problem is solved by a process of the above mentioned type which is characterized in that it comprises the step of flowing the gaseous reagents across at least one of the catalytic beds with substantially radial flow, preferably of centripetal type.

The synthesis gas flow with substantially racial motion permits uniform distribution of the gas striking the catalytic bed, and this is an important feature to ensure uniform distribution of temperature and hence high selectivity in the conversion of methanol to formaldehyde and optimal utilization of the catalytic mass.

In this manner, it is possible to obtain a considerable increase in the productive capacity of the reactor without having to increase the initial methanol concentration in the synthesis gas and hence the risk of explosion of the methanol/oxygen mixture.

Furthermore, thanks to a radial flow of the gaseous reagents across the catalytic beds it is possible to utilize in the best manner the internal volume of the reactor and this helps increase the reaction space and hence production capacity.

Advantageously, the structure of the reactor resulting from this process is technically simpler and more compact with respect to that of the reactor which can be obtained by the process in accordance with the prior art.

In accordance with another aspect of the present invention, the process allows performance of cooling of at least part of a hot gas flow coming from at least one of the catalytic beds by heat exchange in a heat exchanger arranged in the center of the reactor and extending along a longitudinal axis thereof.

In this manner, it is possible to optimize utilization of the internal volume of the reactor to reduce to a minimum the spaces between consecutive catalytic beds. So doing the reaction space inside the synthesis reactor and hence its production capacity is further increased and at the same time the structure of the reactor is made still more compact and simple.

In a preferred embodiment of the process according to the present invention, the oxygen fed to the synthesis reactor is divided in at least two portions, with each being fed to distinct catalytic beds.

Specifically, the present process also calls for the step of injecting into the gas flow coming from at least one of the catalytic beds, a gaseous or liquid flow comprising oxygen.

The intermediate inlet of oxygen into the gas flow traversing the reactor permits achievement of a dual advantage.

On the one hand, it is possible to reduce the oxygen concentration in the reaction gas flow fed to the first catalytic bed to permit increase of the initial methanol concentration while the mixture of the two reagents remains below the explosive limit.

On the other hand, the oxygen thus apportioned in the catalytic beds allows keeping the catalyst constantly in the oxidized state to protect it from possible losses of activity. This phenomenon is generally found at the final step of the oxidation reaction when the oxygen concentration falls below a certain threshold such as for example 3-4% a by volume.

In addition, the process according to the present invention comprises advantageously the step of extracting from the reactor at least part of a gas flow coming from at least one of the catalytic beds.

In this manner it is possible to obtain a gaseous formaldehyde flow coming from the outlet of the synthesis reactor substantially free from methanol and suitable for direct employment for the required uses, for example resin production, and one or more intermediate gaseous flows comprising formaldehyde and methanol useful for the direct preparation of aqueous formaldehyde solutions in which the methanol in concentrations of 7–12% acts as a polymerization inhibitor.

The characteristics and advantages of the present invention are set forth in the description of an embodiment thereof given below by way of non-limiting example with reference to the annexed drawings.

DETAILED DESCRIPTION OF A PREFERRED EMBODIMENT

Figure 1:
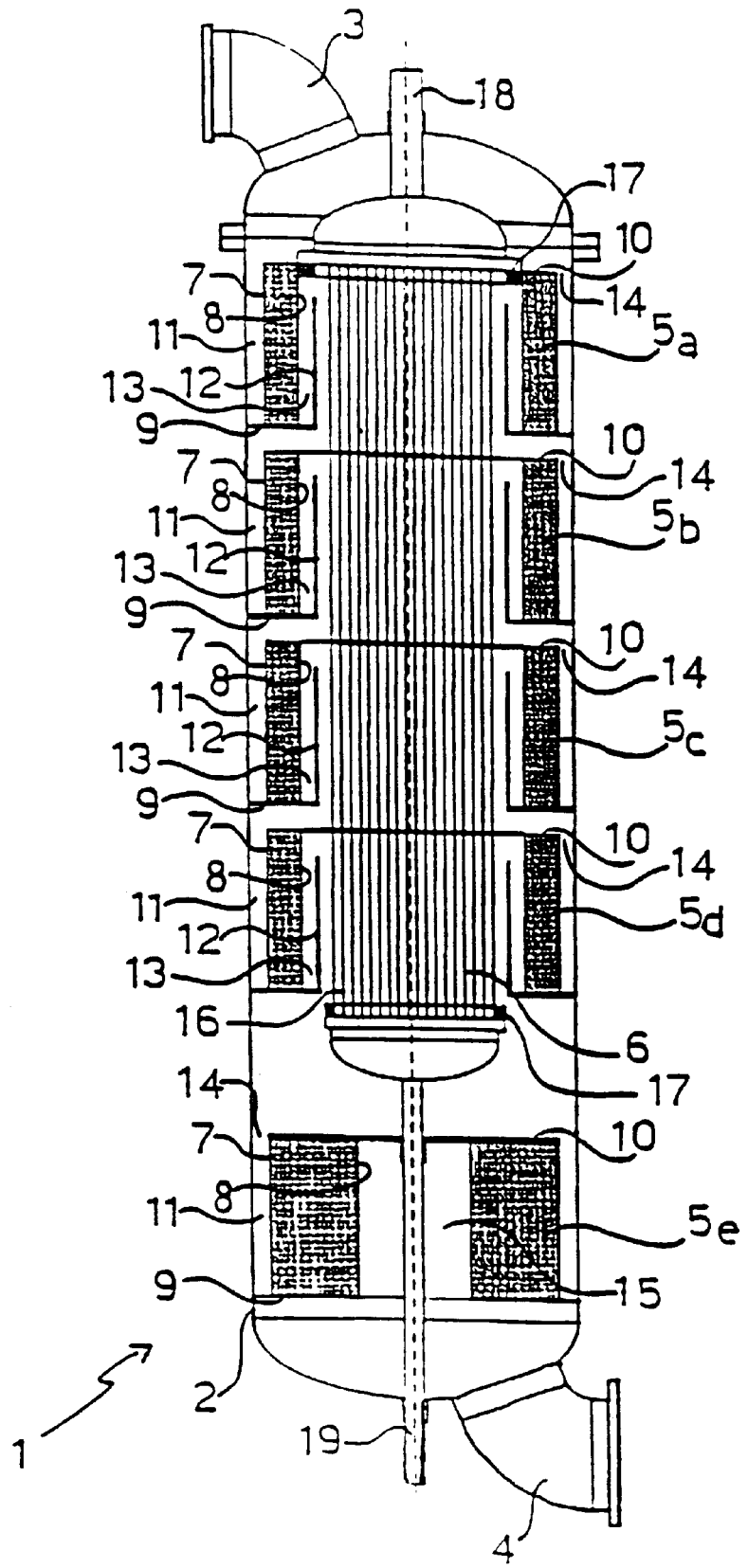
FIG. 1 shows a longitudinal cross section view of a reactor for heterogeneous exothermic synthesis of the formaldehyde for implementation of the process according to the present invention.
Figure 2:
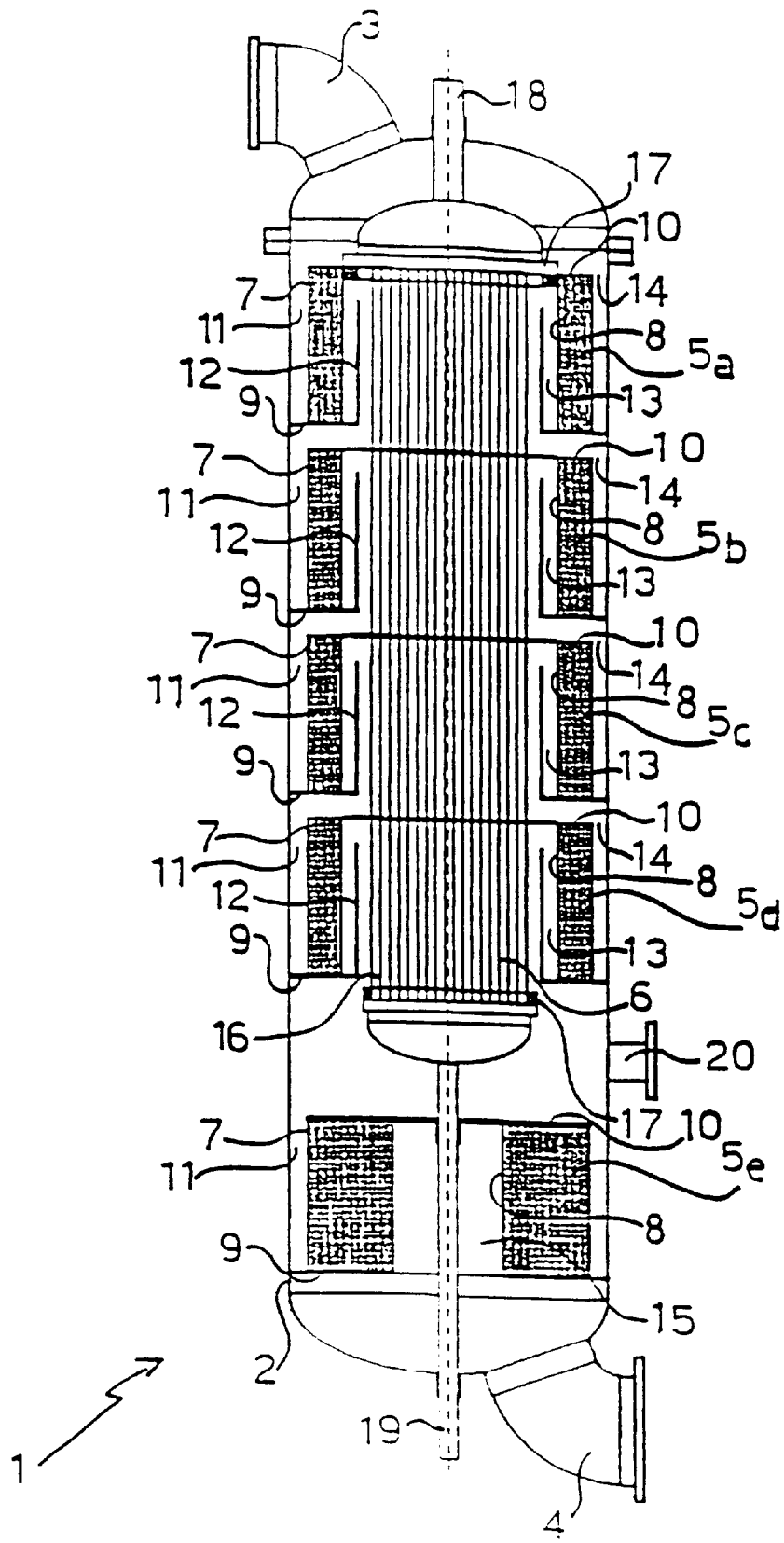
FIG. 2 shows a longitudinal cross section view of an alternative embodiment of the reactor of FIG. 1.

With reference to FIGS. 1 and 2, reference number 1 indicates as a whole a reactor for the heterogeneous exothermic synthesis of the formaldehyde at low pressure (1–3 bar absolute) and high temperature (200–350° C.).

The reactor 1 comprises a vertical tubular shell 2 equipped at its ends with openings 3 and 4 respectively for input of the gaseous reagents appropriately preheated and outlet of the reaction products.

The reagents pass through the reactor 1 in the form of a gaseous phase comprising methanol and excess oxygen.

In the shell 2 are supported in mutually spaced relationship a plurality of superimposed catalytic beds 5a–5e, annular in shape, and a heat exchanger 6 arranged in the center of the reactor 1 and extending along its longitudinal axis.

The catalytic beds 5a–5e are filled with granular catalyst of the type with a base of Fe—Mo, for example of ferric molybdate with possible additions of elements such as for example Mn, Cr, Ti or Co.

The catalytic beds 5a–5e comprise opposing gas permeable side walls 7 and 8 delimited below and above by an annular bottom 9 impermeable to the gas and an annular cover 10 impermeable to the gas, respectively.

In accordance with the process according to the present invention, the gaseous reagents comprising methanol and excess oxygen are made to flow across at least one of the catalytic beds 5a–5e with a substantially radial flow.

In this manner, the catalytic mass contained in the beds is struck uniformly by the gas flow to obtain uniform temperature distribution and hence high selectivity in the conversion of methanol to formaldehyde and optimal utilization of the catalytic mass, with the advantage of an increase in the production capacity of the synthesis reactor.

In a further embodiment of the present process, not shown, the gaseous flow crossing the catalytic beds could be of the axial-radial type. In this case the top cover 10 of the catalytic beds 5a–5e would not be used or would be made gas permeable.

The bottom 9 extends at one end to the internal wall of the shell 2 with which it defines a hollow space 11 for gas inlet to the catalytic beds 5a–5e.

In some of the catalytic beds 5a–5d, for example catalytic bed 5b, the bottom 9 extends also to an annular baffle 12 arranged between the catalytic bed 5b and the heat exchanger 6. There is thus defined a hollow space 13 for outlet of gas from the catalytic bed 5b, in fluid communication, through the opening 14, with the heat exchanger 6 and the hollow space 11 for gas inlet of the following catalytic bed 5c.

At the outlet from the catalytic bed 5e there is provided a chamber 15 for collection of the reaction products in fluid communication with the opening 4 for their expulsion from the reactor 1.

Thanks to this particular configuration of the reactor of the present invention it is possible to carry out the process according to the present invention with a step in which the synthesis gas is made to flow across the catalytic beds 5a–5e with a substantially radial flow of the centripetal type from the outside towards the inside of the reactor 1.

The synthesis gas added to the reactor 1 through the opening 3 for gas inlet flows in a first hollow space 11 and cross radially the first catalytic bed 5a to then collect in the hollow space 13, from which it is made to pass—through the opening 14—to the hollow space 11 for gas inlet of the following catalytic bed 5b. The synthesis gas flows in a similar manner through the remaining catalytic beds 5b–5e to then collect in the chamber 15 and come out of the reactor 1 through the opening 4 for gas outlet.

The oxidation reaction of the methanol is carried out in the catalytic beds 5a–5e by successive steps in series, in each of these the degree of conversion is limited to values preferably not higher than 25% of the total quantity of methanol fed to the synthesis reactor 1.

This control of the degree of conversion of the methanol in the individual catalytic beds is advantageously obtained by appropriately limiting the volume of catalyst of each bed.

The synthesis reaction in the catalytic beds 5a–5e takes place under adiabatic conditions without removal of the heat developed during the passage of the gaseous reagents across the catalytic mass. The reaction heat will then go to increase the temperature of the synthesis gas coming from each of the catalytic beds 5a–5e.

The temperature increase of the gaseous mixture in the catalytic bed is proportionate to the quantity of oxidized methanol, which is therefore held within values such as to not cause development in the catalytic bed of excessively high temperatures, for example higher than 330–350° C., which would be detrimental to the good progress of the conversion reaction of methanol into formaldehyde and to the useful life of the catalyst.

Between a catalytic bed 5a–5d and the next 5b–5e the gaseous reagents are made to pass through the heat exchanger 6 on the shell side and are cooled by means of heat exchange to a temperature such that the oxidation reaction can resume spontaneously when the gas comprising methanol and oxygen comes into contact with the catalyst of the following bed 5b–5e and generally this temperature is between 200 and 250° C.

The heat exchanger 6 is advantageously of the tube nest type comprising a plurality of tubes 16 held in fixed position by two tube plates 17 arranged at their ends.

The cooling fluid which removes the reaction heat is let into the reactor 1 through the inlet duct 19 in fluid communication with the lower tube plate 17, and thence made to pass internally to the tubes 16 to then come out of the reactor 1 appropriately heated through the outlet duct 18 in fluid communication with the upper tube plate 17.

Generally, the cooling fluid consists of a diathermic mineral or synthetic oil, a mixture of melted salts, an evaporating liquid such as Dowtherm or a gas. Preferably superheated or evaporating water is used so as to produce steam which is useful in an industrial plant.

By providing the tube nest with tubes 16 of the so-called low-finned type, the dimensions of the heat exchanger 6 can be considerably reduced providing the advantage of greater reaction space and hence an increase in the productive capacity of the synthesis reactor.

The gaseous flow coming from the last catalytic bed 5e is not cooled but is made available at its maximum temperature for the purpose of preheating the fresh gas to be fed to the first catalytic bed 5a. The heat exchange between the hot gaseous flow and the cold gaseous reagents can take place in a heat exchanger or a preheater, of known type and therefore not shown, arranged outside the shell 2 or inside it.

As an alternative, inside the reactor according to the present invention there can be arranged a single heat exchanger 6 extending centrally along all the catalytic beds 5a–5e for cooling of the hot gas flow emerging therefrom.

In another alternative embodiment (not shown), the heat exchanger can be arranged outside the shell 2. In this case the flow of the synthesis gas across the catalytic beds will be preferably of the radial type from the interior towards the exterior.

Advantageously, the reactor 1 according to the present invention comprises a distributor (not shown) of a gaseous or liquid flow comprising oxygen and supported in the shell 2 between at least two consecutive catalytic beds 5a–5e.

These distributors are arranged between consecutive catalytic beds near the hollow space 11 for gas inlet.

In this manner, it is possible to implement the process according to the present invention with the further step of enriching the gaseous flow passing through the reactor 1 with a steam comprising oxygen, for example air. So doing it is possible to perform an optimal metering of the oxygen into the gaseous flow traversing the reactor 1 to thus make possible an increase both of the total quantity of methanol fed to the reactor and the initial concentration of methanol in the synthesis gas fed to the first catalytic bed. In addition, there is obtained a constant oxidation of the catalyst contained in the catalytic beds 5a–5e.

The oxygen fed to the synthesis gas in gaseous form has preferably a temperature between 0 and 250°.

Advantageously the oxygen is fed to the synthesis gas in liquid form so as to fulfill the auxiliary function of heat removal from the hot gas flow coming from a catalytic bed to cool it.

The presence of this cooling will permit reduction or even elimination of the heat exchanger 6.

Preferably, the fluid comprising oxygen is fed in at the inlet to the penultimate catalytic bed 5d and/or at the inlet to the last catalytic bed 5e.

The number and arrangement of the distributors in the shell 2 can in any case be freely varied depending on the specific requirements of the synthesis reactor.

FIG. 2 shows a preferred embodiment of the reactor of FIG. 1.

In accordance with this embodiment, between at least two consecutive catalytic beds are provided means for extracting from the reactor 1 part of the gaseous flow traversing the catalytic beds and comprising formaldehyde and methanol.

In the example of FIG. 2, these means comprise a duct 20 for gas outlet supported in the shell 2 between the catalytic beds 5d and 5e.

In this manner, it is possible to implement the process according to the present invention with the additional step of extracting the formaldehyde progressively as it is produced in the catalytic beds 5a–5e.

Thanks to this step of the process according to the present invention, it is possible to obtain a gas flow coming out of the synthesis reactor 1 substantially free of methanol, and gas flows coming from intermediate zones of the reactor which comprise formaldehyde and methanol useful for the direct preparation of stabilized aqueous formaldehyde solutions.

Advantageously, the step of addition of a flow comprising oxygen and the step of intermediate extraction of a flow comprising formaldehyde are carried out within the same synthesis reactor downstream of one or more catalytic beds.

In accordance with another embodiment of the reactor according to the present invention, part of the gaseous flow coming from a catalytic bed 5a–5d is advantageously conveyed through a bypass duct (not shown) directly into the following catalytic bed 5b–5e without passing through the heat exchanger 6.

In this manner it is possible to influence in a controlled manner the temperature of the gaseous flow fed to the following catalytic bed 5b–5e.

Advantageously, the reactor represented in the examples of FIGS. 1 and. 2 with a plurality of radial catalytic beds and a single central heat exchanger, permits obtaining at the same time a very compact and technically simple structure which would be very economical, and with optimal utilization of the internal volume of the reactor with the advantage of an increase in the reaction space and hence in productive capacity.

In addition, the fact of dividing the reaction space into a plurality of adiabatic catalytic beds connected in series allows optimal control of the progress of the oxidative reaction of the methanol, permitting minimization of the phenomenon of undesirable secondary reactions and extending the useful life of the catalyst By changing the number of the catalytic beds arranged in the reactor of FIG. 2 and the volume of the catalyst contained therein, it is possible to control the reaction while it is taking place to aid for example conversion of the methanol even where the reduced concentration of the reagents would tend to slow it.

Advantageously, the number of the catalytic beds is generally between 4 and 10. Particularly satisfactory results were obtained with reactors having 5 to 6 catalytic beds.

In particular it was found that with a reactor with 5 catalytic beds of the type exemplified in the figures it is possible to limit the degree of conversion of the methanol in each catalytic bed to approximately 20% of the total quantity of methanol fed to the synthesis reactor. In this manner it is possible to obtain in the beds an optimal reaction temperature between 220 and 310° C., which is less than that for example of a reactor having four catalytic beds where the degree of conversion in each bed is approximately 25%, with a resulting increase in the selectivity and hence in the productive capacity of the reactor.

Lastly, thanks to the special simple and compact structure of the reactor according to the present invention, the operations of maintenance and of loading and unloading of the catalytic mass prove to be considerably simpler and faster as compared with the prior art.

In the following examples comparison is made for indicative and non-limiting purposes of the production capacity obtained from some embodiments of a reactor according to the present invention and a reactor according to the prior art.

EXAMPLE 1

The production capacity of a reactor according to the present invention with radial catalytic beds is compared with the production capacity of a reactor of conventional type with axial catalytic beds.

Inside the two reactors examined are arranged in mutually spaced relationship four adiabatic catalytic beds.

The catalytic beds have the following dimensions:

Catalyst volume of 1st bed: 1300 l

Catalyst volume of 2nd bed: 1400 l

Catalyst volume of 3rd bed: 1600 l

Catalyst volume of 4th bed: 2800 l

Operating conditions of the reactors are as follows.

Average pressure: 1.3 ata

Temperature at catalytic bed inlet: 230° C.

Temperature at catalytic bed outlet: 330° C.

Methanol concentration: 6.5% by vol

Oxygen concentration: 8.0% by vol

The total quantity of methanol fed to the two reactors is equivalent to the quantity of methanol fed to the first catalytic bed which is 3130 kg/h.

The methanol is fed to the reactors in gaseous phase and crosses the catalytic beds with axial flow in the case of the conventional reactor and with radial flow in the case of the reactor according to the present invention.

The quantity of formaldehyde produced by the two reactors is shown below.

Conventional reactor: 2720 kg/h

Reactor according to the invention: 2780 kg/h

The dimensions of the reactor are as follows.

Conventional reactor.
  Internal diameter of shell: 3.0 m
  Total height of reactor: 20.0 m Reactor according to the invention.
  Internal diameter of shell: 2.6 m
  Total height of reactor: 8.0 m An increase of 60 kg/h of formaldehyde produced by the reactor according to the present invention corresponds to an increase in the production capacity of 2% which is a very considerable result if considering the drastic reduction in the size of the reactor.

I claim:

1. A process for the heterogeneous exothermic synthesis of formaldehyde in particular in reactors comprising a plurality of adiabatic catalytic beds connected in series, said process comprising the steps of:

feeding gaseous reagents comprising methanol and excess oxygen to a first of said catalytic beds;

causing said gaseous reagents to flow across said adiabatic catalytic beds to subject the methanol to partial oxidation;

wherein said gaseous reagents flow across at least one of the catalytic beds with substantially radial flow.

2. A process according to claim 1, wherein said gaseous reagents flow across at least one of said catalytic beds with axial-radial flow.

3. A process according to claim 1, wherein said substantially radial flow is centripetal.

4. A process according to claim 3, further comprising the step of cooling at least part of a hot gas flow coming from said at least one of the catalytic beds by heat exchange in a heat exchanger arranged centrally to the reactor and extending along a longitudinal axis thereof.

5. A process according to claim 1, wherein the oxygen feed is distributed into at least two portions, each of said portions being fed to distinct catalytic beds.

6. A process according to claim 5, further comprising the step of injecting into a gaseous flow coming from at least one of the catalytic beds, a gaseous or liquid-flow comprising oxygen.

7. A process according to claim 1, further comprising the step of extracting from said reactor at least part of a gaseous flow coming from at least one of the catalytic beds.

* * * * *